US010401358B1

(12) United States Patent
Bradshaw et al.

(10) Patent No.: US 10,401,358 B1
(45) Date of Patent: Sep. 3, 2019

(54) SERODIAGNOSIS OF LYME DISEASE BY USE OF TWO RECOMBINANT PROTEINS IN ELISA

(71) Applicant: Ross Southern Laboratories, Spanish Fork, UT (US)

(72) Inventors: Gary L. Bradshaw, East Layton, UT (US); R. Kelley Thueson, Mapleton, UT (US); Todd Joseph Uriona, Mapleton, UT (US)

( * ) Notice: Subject to any disclaimer, the term of this patent is extended or adjusted under 35 U.S.C. 154(b) by 0 days.

(21) Appl. No.: 15/717,470

(22) Filed: Sep. 27, 2017

Related U.S. Application Data

(60) Provisional application No. 62/495,972, filed on Sep. 30, 2016, provisional application No. 62/495,973, filed on Sep. 30, 2016.

(51) Int. Cl.
*C07K 14/20* (2006.01)
*C07K 14/245* (2006.01)
*G01N 33/569* (2006.01)

(52) U.S. Cl.
CPC ........ *G01N 33/56911* (2013.01); *C07K 14/20* (2013.01); *C07K 14/245* (2013.01); *C07K 2319/70* (2013.01); *G01N 2333/20* (2013.01); *G01N 2333/245* (2013.01); *G01N 2469/20* (2013.01)

(58) Field of Classification Search
CPC .................. C12Q 1/6804; C12Q 1/689; C12Q 2537/125; C12Q 2563/131; C12Q 2563/143; G01N 33/56911; G01N 2333/20; G01N 2458/10; G01N 2001/4038; G01N 2469/20; C07K 14/20; C07K 2319/40
See application file for complete search history.

(56) References Cited

U.S. PATENT DOCUMENTS

| 6,437,116 B1 | 8/2002 | Norris et al. |
|---|---|---|
| 6,475,492 B1 | 11/2002 | Philipp et al. |
| 6,719,983 B2 | 4/2004 | Norris et al. |
| 6,740,744 B2 | 5/2004 | Norris et al. |
| 6,878,816 B2 | 4/2005 | Norris et al. |
| 7,135,176 B2 | 11/2006 | Norris et al. |

(Continued)

FOREIGN PATENT DOCUMENTS

WO    WO 2015024319    *    6/2015    ............. C12Q 1/689

OTHER PUBLICATIONS

Centers for Disease Control and Prevention National Center for Emerging and Zoonotic Infectious Diseases (NCEZID) Division of Vector-Borne Diseases (DVBD), Two-tiered Testing Decision Tree/ Two-tiered Testing for Lyme Disease, https://www.cdc.gov/lyme/healthcare/clinician_twotier.html, Nov. 15, 2011.

(Continued)

*Primary Examiner* — Jana A Hines
(74) *Attorney, Agent, or Firm* — Clayton Howarth, P.C.

(57) ABSTRACT

Two *Borrelia burgdorferi* recombinant proteins were expressed in *E. coli*. These two proteins were generated from (a) the full length dbpA gene combined with the invariable region 6 of the VlsE gene (dbpA/C6), and (b) the full length OspC gene combined with the coding sequence for amino acids 1-121 of the *E. coli* maltose binding protein gene (OspC/MBP). Methods of using these recombinant proteins for detecting anti-*Borrelia burgdorferi* antibodies in patient sera and diagnosis of Lyme Disease are described.

Figure 2:
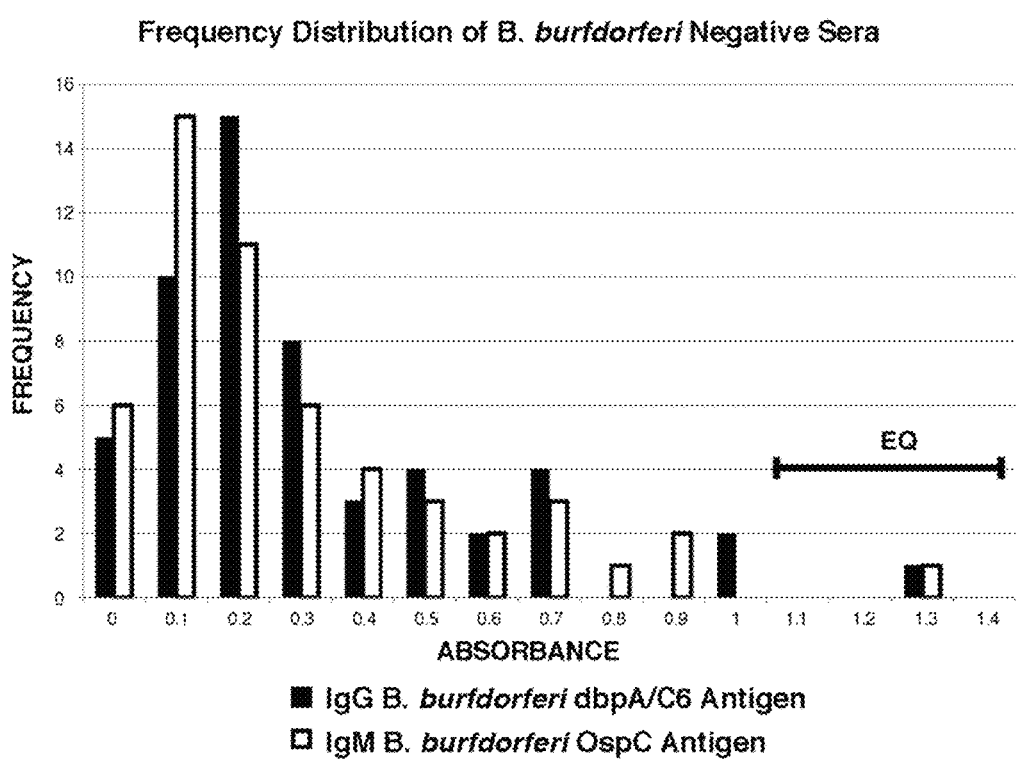

4 Claims, 2 Drawing Sheets
Specification includes a Sequence Listing.

(56) References Cited

U.S. PATENT DOCUMENTS

| | | |
|---|---|---|
| 7,785,597 B2 | 8/2010 | Norris et al. |
| 8,071,109 B2 | 12/2011 | Norris et al. |
| 8,354,240 B2 | 1/2013 | Norris et al. |
| 9,212,218 B2 | 12/2015 | Norris et al. |

OTHER PUBLICATIONS

Centers for Disease Control and Prevention National Center for Emerging and Zoonotic Infectious Diseases (NCEZID) Division of Vector-Borne Diseases (DVBD), Two-step Laboratory Testing Process, https://www.cdc.gov/lyme/diagnosistesting/labtest/twostep/index.html, Mar. 26, 2015.

* cited by examiner

Figure 1A

Figure 1B

SEQUENCE LISTING

<160> NUMBER OF SEQ ID NOS: 13

<210> SEQ ID NO 1
<211> LENGTH: 33
<212> TYPE: DNA
<213> ORGANISM: Borrelia burgdorferi

<400> SEQUENCE: 1
ggatccctcg agatgattaa atgtaataat aaa                                33

<210> SEQ ID NO 2
<211> LENGTH: 33
<212> TYPE: DNA
<213> ORGANISM: Borrelia burgdorferi

<400> SEQUENCE: 2
aagcttctgc aggttatttt tgcattttc atc                                33

<210> SEQ ID NO 3
<211> LENGTH: 33
<212> TYPE: DNA
<213> ORGANISM: Borrelia burgdorferi

<400> SEQUENCE: 3
ggatccctcg agatgaaaaa gaatacatta agt                                33

<210> SEQ ID NO 4
<211> LENGTH: 33
<212> TYPE: DNA
<213> ORGANISM: Borrelia burgdorferi

<400> SEQUENCE: 4
aagcttctgc agaggttttt ttggactttc tgc                                33

<210> SEQ ID NO 5
<211> LENGTH: 33
<212> TYPE: DNA
<213> ORGANISM: Borrelia burgdorferi

<400> SEQUENCE: 5
ctcgagctgc agatgaagaa ggatgatcag att                                33

<210> SEQ ID NO 6
<211> LENGTH: 33
<212> TYPE: DNA
<213> ORGANISM: Borrelia burgdorferi

<400> SEQUENCE: 6
gaattcggat ccaccatcct tcacagcaaa ctt                                33

<210> SEQ ID NO 7
<211> LENGTH: 33
<212> TYPE: DNA
<213> ORGANISM: Escherichia coli

<400> SEQUENCE: 7
ctgcagctcg agatgaaaat cgaagaaggt aaa                                33

<210> SEQ ID NO 8
<211> LENGTH: 33
<212> TYPE: DNA
<213> ORGANISM: Escherichia coli

<400> SEQUENCE: 8
gaattcctgc agcagatctt tgttataaat ctg         33

<210> SEQ ID NO 9
<211> LENGTH: 26
<212> TYPE: PRT
<213> ORGANISM: Borrelia burgdorferi

<400> SEQUENCE: 9

Cys Met Lys Lys Asp Asp Gln Ile Ala Ala Ala Met Val Leu Arg Gly
1               5                   10                  15

Met Ala Lys Asp Gly Gln Phe Ala Leu Lys
            20                  25

<210> SEQ ID NO 10
<211> LENGTH: 244
<212> TYPE: PRT
<213> ORGANISM: Borrelia burgdorferi
<220> FEATURE:
<221> NAME/KEY: DOMAIN
<222> LOCATION: (1)..(193)
<223> OTHER INFORMATION: B. burgdorferi DbpA
<220> FEATURE:
<221> NAME/KEY: DOMAIN
<222> LOCATION: (194)..(219)
<223> OTHER INFORMATION: B. burgdorferi C6

<400> SEQUENCE: 10

His His His His His His Leu Glu Met Ile Lys Cys Asn Asn Lys Thr
1               5                   10                  15

Phe Asn Asn Leu Leu Lys Leu Thr Ile Leu Val Asn Leu Leu Ile Ser
            20                  25                  30

Cys Gly Leu Thr Gly Ala Thr Lys Ile Arg Leu Glu Arg Ser Ala Lys
        35                  40                  45

Asp Ile Thr Asp Glu Ile Asp Ala Ile Lys Lys Asp Ala Ala Leu Lys
    50                  55                  60

Gly Val Asn Phe Asp Ala Phe Lys Asp Lys Thr Gly Ser Gly Val
65                  70                  75                  80

Ser Glu Asn Pro Phe Ile Leu Glu Ala Lys Val Arg Ala Thr Val
                85                  90                  95

Ala Glu Lys Phe Val Ile Ala Ile Glu Glu Ala Thr Lys Leu Lys
            100                 105                 110

Glu Thr Gly Ser Ser Gly Glu Phe Ser Ala Met Tyr Asp Leu Met Phe
        115                 120                 125

Glu Val Ser Lys Pro Leu Gln Lys Leu Gly Ile Gln Glu Met Thr Lys
    130                 135                 140

Thr Val Ser Asp Ala Ala Glu Glu Asn Pro Pro Thr Thr Ala Gln Gly
145                 150                 155                 160

Val Leu Glu Ile Ala Lys Lys Met Arg Glu Lys Leu Gln Arg Val His
                165                 170                 175

Thr Lys Asn Tyr Cys Thr Leu Lys Lys Lys Glu Asn Ser Thr Phe Thr
            180                 185                 190

Asp Glu Lys Cys Lys Asn Asn Leu Gln Met Lys Lys Asp Asp Gln Ile
        195                 200                 205

Ala Ala Ala Ile Ala Leu Arg Gly Met Ala Lys Asp Gly Lys Phe Ala
    210                 215                 220

```
Val Lys Asp Gly Ser Pro Gly Thr Glu Leu Glu Phe Ile Asp Asp Ile
225                 230                 235                 240

Thr Ser Arg Arg
```

<210> SEQ ID NO 11
<211> LENGTH: 359
<212> TYPE: PRT
<213> ORGANISM: Borrelia burgdorferi
<220> FEATURE:
<221> NAME/KEY: DOMAIN
<222> LOCATION: (1)..(122)
<223> OTHER INFORMATION: E. coli maltose binding protein
<220> FEATURE:
<221> NAME/KEY: DOMAIN
<222> LOCATION: (123)..(332)
<223> OTHER INFORMATION: B. burgdorferi OspC

<400> SEQUENCE: 11

```
His His His His His His Leu Glu Met Lys Ile Glu Glu Gly Lys Leu
1               5                   10                  15

Val Ile Trp Ile Asn Gly Asp Lys Gly Tyr Asn Gly Leu Ala Glu Val
            20                  25                  30

Gly Lys Lys Phe Glu Lys Asp Thr Gly Ile Lys Val Thr Val Glu His
        35                  40                  45

Pro Asp Lys Leu Glu Glu Lys Phe Pro Gln Val Ala Ala Thr Gly Asp
    50                  55                  60

Gly Pro Asp Ile Ile Phe Trp Ala His Asp Arg Phe Gly Gly Tyr Ala
65                  70                  75                  80

Gln Ser Gly Leu Leu Ala Glu Ile Thr Pro Asp Lys Ala Phe Gln Asp
                85                  90                  95

Lys Leu Tyr Pro Phe Thr Trp Asp Ala Val Arg Tyr Asn Gly Lys Leu
            100                 105                 110

Ile Ala Tyr Pro Ile Ala Val Glu Ala Leu Ser Leu Ile Tyr Asn Lys
        115                 120                 125

Asp Leu Leu Gln Met Lys Lys Asn Thr Leu Ser Ala Ile Leu Met Thr
    130                 135                 140

Leu Phe Leu Phe Ile Ser Cys Asn Asn Ser Gly Lys Asp Gly Asn Thr
145                 150                 155                 160

Ser Ala Asn Ser Ala Asp Glu Ser Val Lys Gly Pro Asn Leu Thr Glu
                165                 170                 175

Ile Ser Lys Lys Ile Thr Asp Ser Asn Ala Val Leu Leu Ala Val Lys
            180                 185                 190

Glu Val Glu Ala Leu Leu Ser Ser Ile Asp Glu Ile Ala Ala Lys Ala
        195                 200                 205

Ile Gly Lys Lys Ile His Gln Asn Asn Gly Leu Asp Thr Glu Asn Asn
    210                 215                 220

His Asn Gly Ser Leu Leu Ala Gly Ala Tyr Ala Ile Ser Thr Leu Ile
225                 230                 235                 240

Lys Gln Lys Leu Asp Gly Leu Lys Asn Glu Gly Leu Lys Glu Lys Ile
                245                 250                 255

Asp Ala Ala Lys Lys Cys Ser Glu Thr Phe Thr Asn Lys Leu Lys Glu
            260                 265                 270

Lys His Thr Asp Leu Gly Lys Glu Gly Val Thr Asp Ala Asp Ala Lys
        275                 280                 285

Glu Ala Ile Leu Lys Thr Asn Gly Thr Lys Thr Lys Gly Ala Glu Glu
    290                 295                 300
```

Leu Gly Lys Leu Phe Glu Ser Val Glu Val Leu Ser Lys Ala Ala Lys
305                 310                 315                 320

Glu Met Leu Ala Asn Ser Val Lys Glu Leu Thr Ser Pro Val Val Ala
                325                 330                 335

Glu Ser Pro Lys Lys Pro Gly Ser Pro Gly Thr Glu Leu Glu Phe Ile
                340                 345                 350

Asp Asp Ile Thr Ser Arg Arg
        355

<210> SEQ ID NO 12
<211> LENGTH: 741
<212> TYPE: DNA
<213> ORGANISM: Borrelia burgdorferi

<400> SEQUENCE: 12

| | | |
|---|---|---|
| atgcatcatc atcatcatca tctcgagatg attaaatgta ataataaaac ttttaacaat | 60 |
| ttacttaaac taactatact tgttaaccta cttatatcat gtggactaac aggagcaaca | 120 |
| aaaattagat tagaacgaag cgctaaagac attacagatg aaatagatgc aattaaaaaa | 180 |
| gacgctgctc ttaagggcgt aaattttgat gcctttaaag ataaaaaaac gggtagtggg | 240 |
| gtatcagaaa atccattcat acttgaagca aaagtgcgag ctactacagt agcggaaaaa | 300 |
| ttcgtaatag caatagaaga ggaagctact aaactcaaag aaactggaag tagtggtgaa | 360 |
| ttttcagcaa tgtatgattt aatgtttgaa gtctcaaaac cattacaaaa attgggaata | 420 |
| caagagatga caaaaacagt ctcagatgca gctgaagaga atcctccaac tacagctcaa | 480 |
| ggagtgcttg aaattgcaaa aaaaatgaga gaaaaattac aaagggttca tacaaaaaac | 540 |
| tactgcaccc ttaaaagaa ggaaaattct acttttactg atgaaaaatg caaaataac | 600 |
| ctgcagatga gaaggatga tcagattgct gctgctattg ctttgagggg gatggctaag | 660 |
| gatggaaagt ttgctgtgaa ggatggtgga tccccgggta ccgagctcga attcatcgat | 720 |
| gatatcatta catcccggcg g | 741 |

<210> SEQ ID NO 13
<211> LENGTH: 1083
<212> TYPE: DNA
<213> ORGANISM: Borrelia burgdorferi

<400> SEQUENCE: 13

| | | |
|---|---|---|
| atgcatcatc atcatcatca tctcgagatg aaaatcgaag aaggtaaact ggtaatctgg | 60 |
| attaacggcg ataaaggcta taacggtctc gctgaagtcg gtaagaaatt cgagaaagat | 120 |
| accggaatta aagtcaccgt tgagcatccg gataaactgg aagagaaatt cccacaggtt | 180 |
| gcggcaactg gcgatggccc tgacattatc ttctgggcac acgaccgctt tggtggctac | 240 |
| gctcaatctg gcctgttggc tgaaatcacc ccggacaaag cgttccagga caagctgtat | 300 |
| ccgtttacct gggatgccgt acgttacaac ggcaagctga ttgcttaccc gatcgctgtt | 360 |
| gaagcgttat cgctgattta taacaaagat ctgctgcaga tgaaaagaa tacattaagt | 420 |
| gcaatattaa tgactttatt tttatttata tcttgtaata attcagggaa agatgggaat | 480 |
| acatctgcaa attctgctga tgagtctgtt aaagggccta atcttacaga ataagtaaa | 540 |
| aaaattacgg attctaatgc ggttttactt gctgtgaaag aggttgaagc gttgctgtca | 600 |
| tctatagatg aaattgctgc taagctatt ggtaaaaaaa tacaccaaaa taatggtttg | 660 |
| gataccgaaa ataatcacaa tggatcattg ttagcgggag cttatgcaat atcaacccta | 720 |
| ataaacaaa aattagatgg attgaaaaat gaaggattaa aggaaaaaat tgatgcggct | 780 |

```
aagaaatgtt ctgaaacatt tactaataaa ttaaaagaaa aacacacaga tcttggtaaa      840
gaaggtgtta ctgatgctga tgcaaaagaa gccattttaa aaacaaatgg tactaaaact      900
aaaggtgctg aagaacttgg aaaattattt gaatcagtag aggtcttgtc aaaagcagct      960
aaagagatgc ttgctaattc agttaaagag cttacaagcc ctgttgtggc agaaagtcca     1020
aaaaaacctg gatccccggg taccgagctc gaattcatcg atgatatcat tacatcccgg     1080
cgg                                                                   1083
```

SERODIAGNOSIS OF LYME DISEASE BY USE OF TWO RECOMBINANT PROTEINS IN ELISA

CROSS-REFERENCE TO RELATED APPLICATIONS

This application claims the benefit of U.S. Provisional Application No. 62/495,972, filed Sep. 30, 2016, and U.S. Provisional Application No. 62/495,973, filed Sep. 30, 2016, both of which are hereby incorporated by reference herein in their entireties, including but not limited to those portions that specifically appear hereinafter, the incorporation by reference being made with the following exception: In the event that any portion of the above-referenced provisional applications is inconsistent with this application, this application supersedes the above-referenced provisional applications.

STATEMENT REGARDING FEDERALLY SPONSORED RESEARCH OR DEVELOPMENT

Not applicable.

BACKGROUND OF THE INVENTION

This invention relates to diagnosis of Lyme disease. More particularly, this invention relates to improved serodiagnostic performance for Lyme disease by use of two recombinant proteins in ELISA as compared to standardized two-tier testing.

Lyme disease (LD) continues to be the most common vector-borne disease in North America, Hyde J A, *Borrelia burgdorferi* Keeps Moving and Carries on: A Review of Borrelial Dissemination and Invasion, Front. Immunol. 8:114 (2017), with increasing incidence in the United States and Canada, Waddell L A, Greig J, Mascarenhas M, Shannon H, Lindsay R, Ogden N, The Accuracy of Diagnostic Tests for Lyme Disease in Humans, A Systematic Review and Meta-Analysis of North American Research. PLOS ONE. DOI:10.1371/journal.pone.0168613 (2016). The primary agent of LD in North America is the spirochete *Borrelia burgdorferi* sensu stricto which is transmitted chiefly by the tick vectors *Ixodes scapularis* and *I. pacificus*, Shapiro E D, *Borrelia burgdorferi* (Lyme Disease), Pediatr. Rev. 35:500-509 (2014). The diagnosis of LD is based on patient history, clinical presentation, and serology, Hyde, supra; Shapiro, supra. The observation of erythema migrans (EM), which is present in 70-80% of early LD patients, Id., is very important in the detection and diagnosis of this stage of disease and is considered pathognomonic in endemic areas, Seriburi V, Ndukwe N, Chang Z, Cox M E, Wormset G P, High Frequency of False Positive IgM immunoblots for *Borrelia burgdorferi* in Clinical Practice, CMI Clin. Microbiol. Infec. 18:1236-1240 (2012). Direct detection of the spirochete, either by culture or by PCR amplification of *Borrelia* genes, is often unreliable due to the small number of organisms present in any sample or stage of infection. Waddell, et al., supra; Shapiro, supra. Therefore, serology remains the most important confirmatory step in the diagnosis of LD. Theel E S, The Past, Present, and (Possible) Future of Serologic Testing for Lyme Disease, J. Clin. Microbiol. 54:191-1196 (2016). As it is with many infectious diseases, early detection and confirmation of LD is difficult to establish, but it is crucial in the management of the disease. Early treatment for LD can mitigate or even prevent the complications of late stage illness, which can adversely affect the heart, nervous system, and joints and can persist for months or even years. Strie K, Jones K L, Drouin E E, Li X, Steere A C, *Borrelia burgdorferi* RST1 (OspC Type A) Genotype is Associated with Greater Inflammation and More Severe Lyme Disease, Am. J. Pathol. 178:2726-2739 (2011).

The most reliable serological testing method for the diagnosis of LD, which was recommended by the Center for Disease Control and Prevention (CDC) in 1995, CDC, Recommendations for test performance and interpretation from the second national conference on serologic diagnosis of Lyme disease, Morbidity and Mortality Weekly Report 44:590-591 (1995), continues to be a 2-tiered test method. The first-tier is a screening assay, and is most commonly an enzyme-linked immunosorbent (ELISA) assay, using as the antigens either a whole cell lysate of *B. burgdorferi* or specific recombinant proteins or peptides. Johnson B J B, Laboratory Diagnostic Testing for *Borrelia burgdorferi* Infection, CAB International 73-87 (2011). It is typically of low specificity but high sensitivity. If the first-tier test is negative, the sample is considered to be negative and no further testing is advised. However, if the first-tier test is positive or equivocal it is recommended that second-tier testing be done. The second-tier tests are Western blot assays for both IgG and IgM antibodies. Although they also use whole cell lysates of *B. burgdorferi* or specific recombinant proteins as antigens, they provide higher specificity than the first-tier test due to the algorithms used for interpretation. For Lyme IgM Western blots to be considered positive, at least 2 of 3 bands (p23, p39, or p41) must be determined to be positive. And for Lyme IgG Western blots to be considered positive at least 5 of 10 bands (p18, p23, p28, p30, p39, p41, p45, p58, p66, or p93) must be read as positive. Theel, supra; CDC, supra.

Western blot assays are considered technically complex to perform and are, most often, subjective in their interpretation. Theel, supra; Molins C R, Sexton C, Young J W, Ashton L V, Pappert R, Beard C B, Schriefer M E, Collection and Characterization of Samples for Establishment of a Serum Repository for Lyme Disease Diagnostic Test Development and Evaluation, J. Clin. Microbiol. 52:3755-3762 (2014). In contrast, ELISA assays are relatively straight forward to perform, can be quantitative, and are non-subjective in their interpretation. A purpose of this study was to develop one or two recombinant antigens from *B. burgdorferi* that could be used in the development of a 1-tier ELISA test for the confirmation and diagnosis of LD, and that could yield overall specificities and sensitivities equal to, or better, than those of the 2-tiered method for the detection of *Borrelia*-specific antibodies in human sera.

BRIEF SUMMARY OF THE INVENTION

It is a feature of an illustrative embodiment of the present invention to provide recombinant antigens that can be used in ELISA for detection of *Borrelia*-specific antibodies in human sera. Two recombinant proteins were generated. In the first, the full-length *B. burgdorferi* dbpA coding sequence was spliced to the invariable region 6 (IR6) of the *B. burgdorferi* VlsE coding sequence, which, when expressed in *E. coli*, yielded a dbpA/C6 recombinant protein. In the second, the full-length *B. burgdorferi* OspC coding sequence was spliced to the coding sequence for amino acids 1-121 of the *E. coli* malE (maltose bind protein) gene, which, when expressed in *E. coli*, yielded an OspC/MBP recombinant protein.

Another illustrative embodiment of the invention comprises a dbpA/C6 recombinant protein comprising a *Borrelia burgdorferi* dbpA peptide and a *Borrelia burgdorferi* C6 peptide. This dbpA/C6 recombinant protein may comprise a sequence as set forth as SEQ ID NO:10.

Still another illustrative embodiment of the invention comprises an OspC/MBP recombinant protein comprising a *Borrelia burgdorferi* OspC peptide and an *E. coli* MBP peptide. This OspC/MBP recombinant protein may comprise a sequence as set forth as SEQ ID NO:11. The *E. coli* MBP peptide may comprise amino acids 1-121 of the mature *E. coli* MBP protein.

Yet another illustrative embodiment of the invention comprises a method for detecting anti-*Borrelia burgdorferi* antibodies in a patient, the method comprising:

(a) obtaining a plasma sample from a human patient; and (b) detecting whether anti-*Borrelia burgdorferi* antibodies are present in the plasma sample by contacting the plasma sample with (1) a dbpA/C6 recombinant protein comprising a *Borrelia burgdorferi* dbpA peptide and a *Borrelia burgdorferi* C6 peptide, or (2) an OspC/MBP recombinant protein comprising a *Borrelia burgdorferi* OspC peptide and an *E. coli* MBP peptide, or (3) both the dbpA/C6 recombinant protein and the OspC/MBP recombinant protein, and detecting binding between the anti-*Borrelia burgdorferi* antibodies and the dbpA/C6 recombinant protein, the OspC/MBP recombinant protein, or both the dbpA/C6 recombinant protein and the OspC/MBP recombinant protein.

The dbpA/C6 recombinant protein used in this method may comprise a sequence as set forth as SEQ ID NO:10. The OspC/MBP recombinant protein used in this method may comprise a sequence as set forth as SEQ ID NO:11. In an illustrative embodiment, the OspC/MBP protein comprises amino acids 1-121 of the mature *E. coli* MBP protein.

Another illustrative embodiment of the invention comprises a method of diagnosing Lyme Disease in a patient, the method comprising:

(a) obtaining a plasma sample from a human patient;

(b) detecting whether anti-*Borrelia burgdorferi* antibodies are present in the plasma sample by contacting the plasma sample with (1) a dbpA/C6 recombinant protein comprising a *Borrelia burgdorferi* dbpA peptide and a *Borrelia burgdorferi* C6 peptide, or (2) an OspC/MBP recombinant protein comprising a *Borrelia burgdorferi* OspC peptide and an *E. coli* MBP peptide, or (3) both the dbpA/C6 recombinant protein and the OspC/MBP recombinant protein, and detecting binding between the anti-*Borrelia burgdorferi* antibodies and the dbpA/C6 recombinant protein, the OspC/MBP recombinant protein, or both the dbpA/C6 recombinant protein and the OspC/MBP recombinant protein; and (c) diagnosing the patient with Lyme Disease when the presence of anti-*Borrelia burgdorferi* antibodies in the plasma sample is detected.

In an illustrative embodiment of the invention, detecting whether anti-*Borrelia burgdorferi* antibodies are present in the plasma sample comprises contacting the plasma sample with both the dbpA/C6 recombinant protein and the OspC/MBP recombinant protein. Illustratively, ELISA is used for detecting whether anti-*Borrelia burgdorferi* antibodies are present in the plasma sample. The patient may be a stage I, II, or III Lyme Disease patient. The dbpA/C6 recombinant protein may comprise a sequence as set forth as SEQ ID NO:10. The OspC/MBP recombinant protein may comprise a sequence as set forth as SEQ ID NO:11. The OspC/MBP recombinant protein may comprise amino acids 1-121 of the mature *E. coli* MBP protein.

It is another feature of an illustrative embodiment of the present invention to provide a method for serological confirmation of Lyme Disease comprising detecting anti-*Borrelia* antibodies in serum from a subject using the dspA/C6 and OspC/MBP recombinant proteins in ELISA.

Still another illustrative embodiment of the present invention comprises a solid support to which a recombinant protein is bound. Illustrative solid supports include microtiter plates, polymer membranes, glass beads, and the like. Illustrative recombinant proteins include one or both of dbpA/C6 and OspC/MBP.

BRIEF DESCRIPTION OF THE SEVERAL VIEWS OF THE DRAWINGS

Figures 1A, 1B:
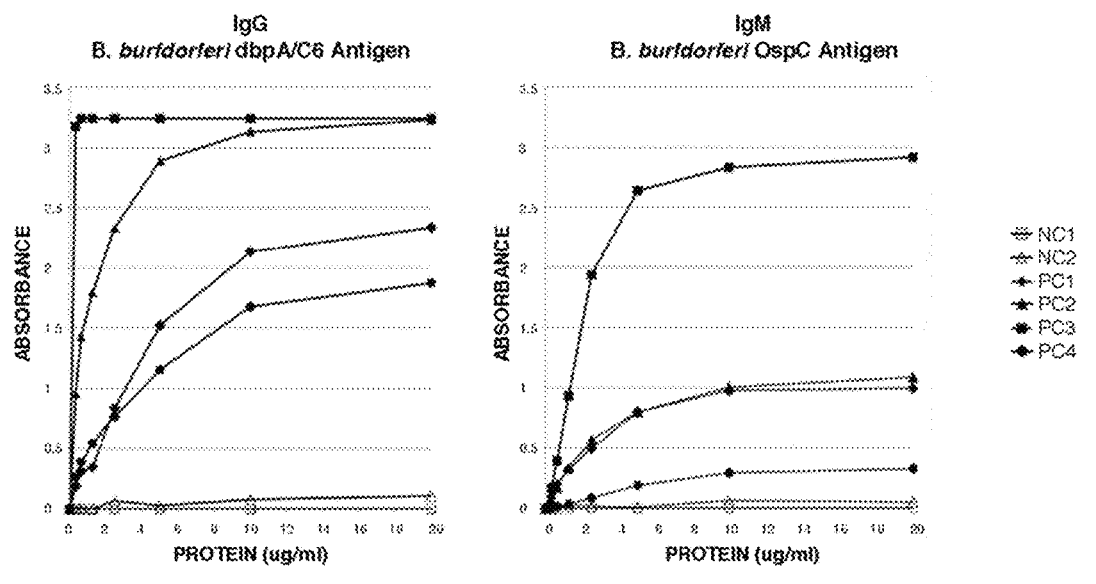

FIGS. 1A and 1B show titration curves for the antigens dbpA/C6 for the detection of IgG and OspC/MBP for the detection of IgM antibodies in an ELISA format. NC=Negative Control. PC=Positive Control. The optimal coating concentration was determined to be about 10 μg/ml, as this was the minimal tested value giving the greatest discrimination between the positive and negative control sera.

FIG. 2 is a frequency distribution graph showing the relation of the cut-off and equivocal values to the 54 negative sera used to generate them. These values were used to declare the positive and negative status of each serum in the comparative tests of the 279 sera premarketing panel from the CDC. The cut-off value was 1.1, and the equivocal range was between 1.1 and 1.4 (black bar).

DETAILED DESCRIPTION

Before the present recombinant proteins and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "a serum" includes a mixture of two or more sera, reference to "an ELISA" includes reference to two or more of such ELISAs, and reference to "the protein" includes reference to a mixture of two or more proteins.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps.

The most reliable test method for the serological confirmation of Lyme Disease (LD) is a 2-tiered method recommended by the CDC in 1995. The first-tier test is a low-specificity ELISA test and the second-tier tests are higher specificity IgG and IgM Western blots. This disclosure describes the selection of two Borrelia burgdorferi-recombinant proteins and evaluation of their performance in a simple 1-tier test for the serological confirmation of LD. These two proteins were generated from (a) the full length dbpA gene combined with the invariable region 6 of the VlsE gene (dbpA/C6) and (b) the full length OspC gene combined with the coding sequence for amino acids 1-121 of the mature E. coli maltose binding protein gene. The expressed dbpA/C6 and the OspC/MBP proteins were useful in detecting anti-Borrelia IgG and IgM antibodies, respectively. A blind study was conducted on a well-characterized panel of 279 human sera from the CDC comparing ELISA tests using these two recombinant antigens with the 2-tiered test method. The two methods (dbpA/C6-OspC/MBP v. 2-tiered) compared equivalently in identifying sera from negative control subjects (99% vs 100% specificity, respectively) and in detecting stage II & III LD patient sera (100% vs 100% sensitivity). However, the dbpA/C6-OspC/MBP ELISA test was markedly better (80% v. 63%) than the 2-tiered test method in detecting anti-Borrelia antibodies in stage I LD patients. These finding suggest that these antigens can be used in a simple 1-tier ELISA assay that is faster to perform, easier to interpret, and less expensive than the 2-tiered test method, and that is better at detecting Borrelia-specific antibodies in patient sera with stage I LD.

Gene Expression and Reactivity of Proteins:

As part of the initial phase of this work, a number of B. burgdorferi proteins, considered to be important in the serology of LD, were generated as recombinant proteins expressed in E. coli. These included dbpA, OspC, p28, p30, p39, p41, p45, p58, p66, p93, and VlsE. Also included in the studies was the synthetic peptide C6 (SEQ ID NO:9), as well as a recombinant fusion proteins that were comprised of both dbpA and C6 (dbpA/C6; SEQ ID NO:10) and of both OspC and E. coli MBP (OspC/MBP; SEQ ID NO:11). Each of these purified antigens was titrated in an ELISA format to demonstrate their specific activity and to determine their optimal coating concentrations. Titration curves for the antigens dbpA/C6 for the detection of IgG and OspC/MBP for the detection of IgM antibodies are shown in FIGS. 1A and 1B. The optimal coating concentration is defined herein as the minimum concentration of antigen yielding maximum discrimination between the positive and negative control sera. For both dbpA/C6 and OspC/MBP, the optimal coating concentration was determined to be approximately 10 µg/ml.

These recombinant proteins varied substantially in their reactivity with Borrelia-specific IgG and IgM antibodies when tested against the LD positive and negative control sera from MarDx Diagnostic, Inc. (Carlsbad, Calif.). The dbpA, VlsE, and dbpA/C6 antigens each showed a high degree of reactivity with IgG anti-Borrelia antibodies, while OspC/MBP, p39, and p41 were very reactive with both IgG and IgM anti-Borrelia antibodies. However, it was observed that p39, p41, and VlsE each also showed a significant degree of reactivity with some of the negative control sera as well (results not shown). Based on these results three recombinant proteins (dbpA, dbpA/C6 and OspC/MBP) were chosen for further evaluation. To directly compare the reactivity of each of these three proteins, along with the synthetic C6 peptide, a panel of 18 LD-positive control sera from MarDx was used. Cut-off and equivocal values were determined using a panel of sera from LD-negative subjects, accumulated to that point in the study, and which were included in each assay. As shown, in these comparison tests only dbpA/C6 identified all of the LD control sera as positive for IgG (Table 1) and only OspC/MBP identified all as positive for IgM (Table 2). Also of note, as shown in Table 1, is that the fusion protein dbpA/C6 elicited a stronger IgG reaction in more than half the sera tested than did the combined results of both of its component parts. Based on these and other similar results, the field of recombinant proteins was narrowed to only two, dbpA/C6 (for the detection of IgG) and OspC/MBP (for the detection of IgM), for more extensive evaluation in blind studies using well-characterized LD serum panels received from the CDC (Fort Collins, Colo.).

TABLE 1

Comparisons of dbpA/C6, dbpA, C6, and OspC/MBP antigens for their ability to detect Borrelia-specific IgG antibodies in LD-positive patient sera

| Sera[a] | dbpA/C6 | dbpA | C6 | OspC/MBP |
|---|---|---|---|---|
| L1 | 2.757[b] P[c] | 0.761 P | 0.445 N | 3.236 P |
| L2 | 3.333 P | 1.800 P | 2.056 P | 3.432 P |
| L3 | 3.190 P | 1.426 P | 3.173 P | 3.403 P |
| L4 | 3.192 P | 2.783 P | 1.501 P | 1.181 N |
| L5 | 1.341 P | 0.186 N | 0.087 N | 3.068 P |
| L6 | 3.359 P | 2.842 P | 0.716 E | 2.942 P |
| L7 | 3.146 P | 2.878 P | 0.418 N | 1.095 N |
| L8 | 3.379 P | 3.379 P | 0.087 N | 3.344 P |
| L9 | 2.672 P | 0.739 P | 0.716 E | 3.166 P |
| L10 | 2.345 P | 0.667 P | 0.433 N | 2.797 P |
| L11 | 3.382 P | 0.421 P | 1.594 P | 2.447 P |
| L12 | 2.149 P | 0.915 P | 0.064 N | 1.344 E |
| L13 | 3.152 P | 1.134 P | 0.381 N | 2.785 P |
| L14 | 3.271 P | 1.521 P | 2.316 P | 3.400 P |
| L15 | 3.182 P | 1.831 P | 2.893 P | 3.403 P |
| L16 | 2.411 P | 0.134 N | 0.125 N | 3.443 P |
| L17 | 3.421 P | 0.228 E | 0.439 N | 3.443 P |
| L18 | 2.576 P | 0.237 E | 0.324 N | 3.421 P |
| LD Neg. | 0.089[d] (0.07)[e] | 0.059 (0.056) | 0.204 (0.129) | 0.460 (0.259) |

[a]L1-L18 = Borrelia-positive sera from MarDx; LD Neg. = Borrelia-negative sera
[b]Absorbance value
[c]P = Positive; N = Negative; E = Equivocal
[d]Mean absorbance value from the determinations of 19 LD-negative sera (except for C6, which was from 6 negative sera)
[e]One standard deviation from the mean

TABLE 2

Comparisons of dbpA/C6, dbpA, and OspC/MBP antigens for their ability to detect Borrelia-specific IgM antibodies in LD-positive sera

| Sera[a] | dbpA/C6 | dbpA | OspC/MBP |
|---|---|---|---|
| L1 | 0.020[b] N[c] | 0.005 N | 0.720 P |
| L2 | 0.156 P | 0.059 N | 2.783 P |
| L3 | 0.215 P | 0.053 N | 3.219 P |
| L4 | 0.015 N | 0.034 N | 0.675 P |
| L5 | 0.020 N | 0.000 N | 1.126 P |
| L6 | 0.046 E | 0.000 N | 0.884 P |

TABLE 2-continued

Comparisons of dbpA/C6, dbpA, and OspC/MBP antigens
for their ability to detect Borrelia-specific IgM
antibodies in LD-positive sera

| Sera[a] | dbpA/C6 | dbpA | OspC/MBP |
|---|---|---|---|
| L7 | 0.042 N | 0.036 N | 0.614 P |
| L8 | 0.016 N | 0.009 N | 0.190 P |
| L9 | 0.019 N | 0.011 N | 0.840 P |
| L10 | 0.014 N | 0.017 N | 0.663 P |
| L11 | 0.021 N | 0.007 N | 1.493 P |
| L12 | 0.000 N | 0.000 N | 0.290 P |
| L13 | 0.085 P | 0.006 N | 1.307 P |
| L14 | 0.162 P | 0.037 N | 2.922 P |
| L15 | 0.287 P | 0.402 P | 3.234 P |
| L16 | 0.177 P | 0.001 N | 2.861 P |
| L17 | 0.151 P | 0.013 N | 3.461 P |
| L18 | 0.221 P | 0.010 N | 1.565 P |
| LD Neg. | 0.008[d] (0.012)[e] | 0.015 (0.036) | 0.049 (0.032) |

[a]L1-L18 = LD-positive sera from MarDx; LD Neg. = LD-negative sera
[b]Absorbance value
[c]P = Positive; N = Negative; E = Equivocal
[d]Mean absorbance value from the determinations of 19 LD-negative sera
[e]One standard deviation from the mean The Comparative Testing of a Panel of Paired LD Patient Acute and Convalescent Sera from the CDC:

A panel of 15 pairs of acute and convalescent sera from physician-diagnosed early Lyme disease patients, Molins et al., supra, was received from the CDC. The IgG and IgM status of each serum had already been determined at the CDC by the 2-tiered method previous to their receipt. These sera were tested for IgG and IgM reactivity using dbpA/C6 and OspC/MBP recombinant proteins, respectively. Cut-off and equivocal values for these tests were determined using a panel of 21 sera from negative control subjects that were accumulated in-house and included in each of the test runs. The individual results of both recombinant proteins, as well as the 2-tiered test, are presented in Table 3 and summarized in Table 4. As shown, the dbpA/C6 and OspC/MBP antigens were successful in identifying a higher percentage of the sera, acute as well as convalescent, as being positive for Lyme specific antibodies than did the 2-tiered system. As shown, one pair of sera was completely negative by either test method.

TABLE 3

Comparison of dbpA/C6 (IgG) and Osp/MBP (IgM) with the
2-tiered method for detecting Lyme-specific antibodies in an
acute and convalescent paired sera panel from the CDC

| dbpA/C6 IgG | OspC/ MBP IgM | Vidas[c] IgG | Marblot[d] IgG | Marblot[d] IgM | 2-tiered IgG | 2-tiered IgM | Serum |
|---|---|---|---|---|---|---|---|
| 0.119[a] N[b] | 0.403 N | E | N | P | N | P | Acute |
| 2.989 P | 1.268 P | P | N | P | N | P | Conv. |
| 3.219 P | 0.955 P | P | N | P | N | P | Acute |
| 3.133 P | 1.494 P | P | N | N | N | N | Conv. |
| 2.918 P | 3.348 P | P | P | P | P | P | Acute |
| 3.169 P | 2.742 P | P | P | P | P | P | Conv. |
| 3.280 P | 1.347 P | P | N | P | N | P | Acute |
| 3.246 P | 1.418 P | P | P | P | P | P | Conv. |
| 0.209 N | 0.100 N | N | N | N | N | N | Acute |
| 0.221 N | 0.106 N | N | N | N | N | N | Conv. |
| 3.075 P | 3.422 P | P | N | P | N | P | Acute |
| 3.057 P | 3.283 P | P | N | P | N | P | Conv. |
| 2.913 P | 1.460 P | P | N | P | N | P | Acute |
| 3.046 P | 0.918 P | P | N | P | N | P | Conv. |
| 3.325 P | 0.219 N | P | P | N | P | N | Acute |
| 3.322 P | 0.372 N | P | P | N | P | N | Conv. |
| 0.130 N | 1.075 P | P | N | N | N | N | Acute |
| 0.000 N | 0.628 E | E | N | N | N | N | Conv. |
| 1.554 P | 0.410 N | P | N | N | N | N | Acute |
| 1.447 P | 0.848 P | P | N | N | N | N | Conv. |
| 3.078 P | 3.420 P | P | P | P | P | P | Acute |
| 3.074 P | 3.185 P | P | P | P | P | P | Conv. |
| 3.094 P | 1.965 P | P | P | N | P | N | Acute |
| 2.503 P | 2.399 P | P | P | N | P | N | Conv. |
| 1.370 P | 1.571 P | P | N | N | N | N | Acute |
| 3.302 P | 3.167 P | P | P | N | P | N | Conv. |
| 1.702 P | 0.669 E | P | P | N | P | N | Acute |
| 3.074 P | 0.728 E | P | P | P | P | P | Conv. |
| 0.861 P | 3.113 P | P | N | P | N | P | Acute |
| 2.187 P | 2.907 P | P | N | P | N | P | Conv. |
| 0.111[e] (0.139)[f] | 0.154[e] (0.149)[f] | | | | | | |

[a]Absorbance value
[b]P = Positive; N = Negative; E = Equivocal
[c]First tier of the 2-tiered method
[d]Second tier of the 2-tiered method
[e]Mean absorbance value from the determinations of 21 LD-negative sera
[f]One standard deviation from the mean

TABLE 4

Summary of the comparative results with the panel of
acute/convalescent sera pairs from Table 3

| | dbpA/C6 - OspC/MBP[a] | 2-Tiered |
|---|---|---|
| | Acute | |
| IgG | 80% (12[b]/15[c])[d] | 33% (5/15) |
| IgM | 67% (10/15)[e] | 53% (8/15) |
| IgG/IgM | 87% (13/15)[e] | 73% (11/15) |
| | Convalescent | |
| IgG | 87% (13/15)[d] | 47% (7/15) |
| IgM | 73% (11/15)[e] | 53% (8/15) |
| IgG/IgM | 87% (13/15)[e] | 73% (11/15) |

[a]DbpA/C6 for detecting IgG and OspC/MBP for detecting IgM
[b]Total sera identified as Lyme positive in group
[c]Total sera in group
[d]Statistically superior
[e]No statistical difference The Comparative Evaluation of a 279 Sera Lyme Premarketing Panel from the CDC.

To test the dbpA/C6 and OspC/MBP recombinant antigens in a larger blind study, the CDC provided a panel of 279 sera derived from Lyme patients and various negative control subjects. Molins et al., supra. Each of these sera was tested by ELISA for IgG antibodies to dbpA/C6 and IgM antibodies to OspC/MBP. Included in each test run were 24 "in-house" as well as MarDx negative control sera from non-LD individuals. After the ELISA test results were obtained and recorded, the CDC provided a table with the identification of each serum, as well as the individual IgG and IgM test result, which it had previously obtained by the 2-tiered method. Eighty nine of these sera were from physician-diagnosed LD positive patients. The remaining 190 sera were from patients with no history of LD. Molins et al., supra. These included 100 sera from healthy individuals (50 from Lyme non-endemic areas and 50 from Lyme endemic areas). It also included 90 sera from patients with diseases that can mimic some symptoms of LD and/or induce cross-reactive antibodies to *Borrelia* antigens, thus complicating an accurate diagnosis. These included 15 sera each from patients with fibromyalgia, mononucleosis, multiple sclerosis, periodontitis, rheumatoid arthritis, and syphilis.

To determine cut-off and equivocal values for this 279 sera panel, the results of 54 sera from non-LD subjects were used. These included the 24 "in-house" and MarDx negative control sera, included in each test run, in combination with the results of 30 randomly selected (using a program from random.org) sera from the 100 healthy endemic and healthy non-endemic group. The inclusion of the 30 randomly selected results was an attempt to increase the accuracy of the cut-off and equivocal values by increasing the number and diversity of the negative sera used to generate them. The results of the 30 randomly selected sera were then omitted from any of the down-stream comparison calculations (leaving 160 of the original 190 negative sera for the comparisons). To show how these 54 LD negative sera were distributed relative to the calculated cut-off and equivocal range values, a frequency distribution graph was created for both IgG and IgM. The cut-off value was set at 3 SDs and the equivocal range was set between 3 and 4 SDs from the mean (FIG. 2). This gave a calculated cut off value for both IgG and IgM of 1.1 and an equivocal range of between 1.1 and 1.4 (black bar on graph). These values occur at the extreme ends of the tails of each curve and as such were positioned to minimize the number of false positive determinations (see discussion below).

Table 5 summarizes the results of all 249 sera (omitting the results of the 30 sera used in the calculations of the cut off and equivocal values) from the 279 sera premarketing panel with regard to their declared clinical status as LD or non-LD subjects. The comparisons are grouped into stage I LD, stage II & III LD, and non-LD categories. The 2-tiered method uses the combined results of both the IgG and IgM Western blot determinations to declare an overall positive or negative status for each serum. When the results using dbpA/C6 (IgG) and OspC/MBP (IgM) antigens are combined, they compare statistically the same with those of the 2-tiered method for identifying LD negative subjects (99% vs 100%) as well as stage II and III LD patient samples (100% vs 100%). However, the combined results of both the dbpA/C6 and OspC/MBP tests were statistically superior to the 2-tiered method in identifying stage I LD patients (80% vs 63%). The data also show that even when considering the dbpA/C6 IgG determinations alone, the results were still equivalent to the 2-tier test in identifying LD-negative control sera (100% vs 100%), and in identifying stage II and III LD patient sera (97% vs 100%), but again statistically better than the 2-tier test in identifying stage I LD patient sera (78% vs 63%).

TABLE 5

Summary of the comparative results with the 279 sera premarketing panel from the CDC

| | dbpA/C6 - OspC/MBP[a] | 2-Tiered |
|---|---|---|
| | Sera from Stage I Lyme Disease | |
| IgG | 78% (46[b]/59[c])[d] | 29% (17/59) |
| IgM | 64% (38/59)[e] | 51% (30/59) |
| IgG/IgM | 80% (47/59)[d] | 63% (37/59) |
| | Sera from Stage II & III Lyme Disease | |
| IgG | 97% (29/30)[e] | 87% (26/30) |
| IgM | 43% (13/30)[e] | 53% (16/30) |
| IgG/IgM | 100% (30/30)[e] | 100% (30/30) |

TABLE 5-continued

Summary of the comparative results with the 279 sera premarketing panel from the CDC

| | dbpA/C6 - OspC/MBP[a] | 2-Tiered |
|---|---|---|
| | Sera from Lyme-Negative Subjects | |
| IgG | 0% (0/160)[e] | 0% (0/160) |
| IgM | 1% (2/160)[e] | 0% (0/160) |

[a]DbpA/C6 for detecting IgG and OspC/MBP for detecting IgM
[b]Total sera identified as Lyme positive in group
[c]Total sera in group
[d]Statistically superior
[e]No statistical difference As mentioned above, at the beginning of the study more than a dozen recombinant *B. burgdorferi* genes, whose encoded proteins were considered to be important in the serology of LD, were cloned, expressed in *E. coli*, and purified. The purpose for making these recombinant proteins was to identify candidate antigens that could be used to develop a simplified assay for the serological confirmation and diagnosis of LD. Each protein, therefore, was carefully screened for its ability to react with IgG or IgM antibodies in human sera which had previously been determined by Western blotting to contain both types of anti-*Borrelia* antibodies. Most of these antigens were quickly eliminated from further study because of poor to moderate reactivity with the control sera. Three of the recombinant proteins (p39, p41, VlsE), which were highly reactive with both IgG and IgM antibodies in LD-positive sera, also showed a high degree of reactivity with certain of the negative control subject samples. To justify eliminating these antigens as possible candidates for continued study, further investigation of their reactivity with LD-negative subject sera was warranted. It seemed conceivable that some of the observed reactions with the sera from LD negative subjects might simply be a result of reactions with *E. coli* proteins that may have co-purified with the recombinant antigens. This possibility was tested in two ways: (a) the LD-negative control sera were absorbed with *E. coli* lysates prior to the performance of ELISA tests using VlsE, p39, or p41 as antigens, and (b) p41 was further purified, to >99%, using isoelectric focusing (IEF). However, neither the absorption studies nor the further purification of p41 resulted in any observable difference in the noted reactivity with the LD negative control sera, indicating that it was not *E. coli* proteins that were involved in these reactions. A more likely explanation was that these reactions were due to cross-reactive antibodies present in these particular negative control subject, possibly generated by exposure to other agents possessing proteins with epitopes that were structurally similar to those found in VlsE, p39, or p41. The ability of an antigen to react with cross-reacting antibodies is a difficult challenge to overcome in trying to develop a simplified serological test, especially one that emphasizes specificity. Therefore, these antigens were also eliminated from further testing. In the evaluation process, two antigens emerged, dbpA and OspC, that were highly reactive with IgG or IgM antibodies in LD positive patient sera, respectively, and that were non-reactive with any of the LD negative control sera.

As previously noted, recombinant OspC had emerged as being a very good antigen for the detection of IgM anti-*Borrelia* antibodies. However, it was expressed in *E. coli* in small amounts, which greatly hindered its purification. In an effort to increase expression of OspC, it was fused with a portion of the *E. coli* malE gene, which codes for maltose binding protein. This generated a fusion protein with expression levels greater than 5-fold over that of unfused OspC, which markedly facilitated its purification. ELISA testing of this OspC/MBP fusion protein showed a small overall increase in its reactivity with *Borrelia* IgM positive patient sera compared to OspC alone, probably reflecting a higher specific activity due to enhanced purification. However, importantly, it also indicated that the fusion with this piece of MBP did not alter the folding of OspC in a manner that observably hindered antibody reactions with specific epitopes. Another important observation using this version of OspC was that no increase in reactions with LD-negative subject sera was noted. This fusion protein, designated as OspC/MBP, was used in all the tests reported in this disclosure.

The receipt of well-characterized panels of Lyme positive and negative sera from the CDC allowed the opportunity to test the two antigens, dbpA/C6 and OspC/MBP, much more extensively. The first of such tests reported herein was those of physician-diagnosed LD patient acute and convalescent serum pairs. For these tests, the only negative sera that could be included for the establishment of cut-off and equivocal values were those that had been accumulated "in-house" to that date and that had been given to us by MarDx. Although specificity could not be determined, the sensitivity of the ELISA reactions using the two recombinant proteins, dbpA/C6 for IgG and OspC/MBP for IgM, exceeded those of the 2-tiered test, for both acute and convalescent sera.

The final panel received from the CDC contained 279 sera. Each was labeled with only a number. After all the tests had been run and the data obtained and recorded, the CDC supplied the key to the panel. The cut-off and equivocal values (calculated from a pool of negative sera as described herein) were set at 3 and 4 standard deviations from the mean, respectively, to emulate the 2-tiered test method in trying to maximize specificity without excessively compromising sensitivity. Seriburi et al., supra. The practical reason for this is that, with millions of Lyme tests conducted each year, even a 1% false positive rate could result in tens of thousands of people annually being unnecessarily treated for LD. Johnson, supra; Theel, supra. Using the established cut-off and equivocal range values to predict a positive or negative status for each serum, a direct comparison was made of the ELISA test using the two recombinant antigens (dbpA/C6 and OspC/MBP) with that of the 2-tiered test method. Besides the dbpA/C6-OspC/MBP ELISA test being simpler to perform and to interpret, the major notable difference between it and the 2-tiered test method was its greater capacity to identify Stage I LD patient sera compared to that of the 2-tiered method. This is significant, because early confirmation of LD in a patient can stimulate the initiation of specific treatment for the disease, thereby lowering the patient's potential risk for developing the debilitating complications associated with the later stages of illness. With regard to early detection of LD, the Vidas IgG ELISA test, used as a screening test in the 2-tiered method, compared equivalently to the dbpA/C6-OspC/MBP ELISA test in identifying stage I LD patient sera. However, a significant disadvantage to the Vidas IgG test is that it also gave Lyme-positive status to 53% (8/15) of the subjects in the mononucleosis group and 87% (13/15) of the subjects in the syphilis group, compared to 7% (1/15) and 0% (0/15), respectively, for the dbpA/C6-OspC/MBP test. The Western blot assays in the 2-tiered test identified all the sera from the subjects in these two groups as anti-*Borrelia* antibody negative.

In summary, this disclosure shows that the two recombinant proteins described herein (dbpA/C6 and OspC/MBP) are excellent antigens for establishing a simple and reliable 1-tier ELISA test for the serological confirmation and diagnosis of LD. Using these antigens, such a test has the specificity of the second-tier Western blot assays of the 2-tiered test method but the sensitivity of the first-tier screening assay. As such, it possibly possesses a greater capacity to identify *Borrelia*-specific antibodies in the serum of patients with Stage I LD and still be highly discriminatory towards the sera of LD-negative subjects. In addition, it is faster and easier to perform, more simple to interpret, and less expensive than the 2-tiered test method.

Example 1

Cloning of *B. burgdorferi* genes: *Borrelia burgdorferi* strain B31 cells were from MarDx Diagnostic, Inc. (Carlsbad, Calif.). *E. coli* BL21(DE3) pLysS One Shot and Top10 Chemically Competent Cells were purchased from Invitrogen Life Technologies (Carlsbad, Calif.).

DNA and RNA were extracted from pelleted *B. burgdorferi* cells using the DNeasy or RNeasy Kits, respectively, from QIAGEN Sciences, Inc. (Germantown, Md.) according to the manufacturer's instructions. Primers for the PCR reactions (Table 6) were purchased from the University of Utah Cores Labs (Salt Lake City, Utah). Each of the primers was 33 nucleotides in length. The first 12 nucleotides at the 5' end of each primer specified restriction sites, and nucleotides 13-33 were specific for the selected gene being amplified. PCR reactions were carried out using the SuperScript III One-Step RT-PCR or the Platinum Taq DNA Polymerase High Fidelity kits from Invitrogen Life Technologies.

TABLE 6

Primers used in the PCR amplification of specific *B. burgdorferi* and *E. coli* genes

| Genes | 5'-Oligonucleotide primers | 3'-Oligonucleotide primers |
|---|---|---|
| dbpA[a] | SEQ ID NO: 1 | SEQ ID NO: 2 |
| OspC[a] | SEQ ID NO: 3 | SEQ ID NO: 4 |
| VlsE[b] | SEQ ID NO: 5 | SEQ ID NO: 6 |
| malE[c] | SEQ ID NO: 7 | SEQ ID NO: 8 |

[a]*B. burgdorferi* genes
[b]IR6 region of the *B. burgdorferi* VlsE gene
[c]*E. coli* maltose binding protein gene PCR amplification of sequences from the dbpA, OspC, and VlsE IR6 genes from *B. burgdorferi*, as well as the *E. coli* maltose binding protein (malE) gene (representing amino acids 1-121 of MBP), yielded PCR products with approximate base-pair sizes, in an agarose gel, corresponding to the expected base pair sizes of 597, 653, 105, and 390 (including primer arms), respectively (not shown). These amplicons were cut with the appropriate restriction enzymes and cloned into the multiple cloning site of an expression vector containing an ampicillin resistance gene, a T7 promoter, and a code for six histidines upstream of the multiple cloning site, in frame with the code for the six histidines. The dbpA coding sequence was cloned by itself as well as in tandem with the VlsE IR6 coding sequence (with VlsE IR6 immediately behind dbpA). The resulting recombinant dbpA/VlsE IR6 coding sequence is set out as SEQ ID NO:12. When expressed in *E. coli* (Example 2), the resulting dbpA/C6 recombinant protein (SEQ ID NO: 10) contained 244 amino acid residues, wherein residues 1-6 were the 6 histidine residues, residues 7-8 were plasmid-specified, residues 9-220 were dbpA-specific, residues 221-226 were C6-specific, and residues 227-244 were plasmid-specified. OspC and malE genes were also cloned in tandem, with the malE directly in front of the OspC. The resulting recombinant ospC/malE coding sequence is set out as SEQ ID NO:13. When expressed in *E. coli* (Example 2), the resulting OspC/MBP recombinant protein (SEQ ID NO:11) contained 359 amino acid residues, wherein residues 1-6 were the 6 histidine residues, residues 7-8 were plasmid-specified, residue 9 was a methionine residue, residues 10-130 were MBP-specific, residues 131-132 were plasmid-specified, residues 133-341 were OspC-specific, and residues 342-359 were plasmid-specified. The expression plasmids containing the dbpA, dbpA/IR6 and OspC genes yielded recombinant proteins dbpA, dbpA/C6, and OspC/MBP of approximate molecular weights of 19 kDa, 21 kDa, and 37 kDa, respectively (not shown).

The C6 peptide (SEQ ID NO:9), the amino acid structure of which was deduced from the invariable region 6 (IR6) of the VlsE gene, Embers, supra, was produced by BIOMATIK (Cambridge, Ontario, Canada).

Example 2

Recombinant Protein Expression and Purification.

Expression plasmid DNA was purified using the QIAfilter Plasmid Midi kit from Qiagen (Valencia, Calif.), transformed into chemically competent BL-21(DE3) pLysS cells as directed by the manufacturer (Invitrogen Life Technologies, Carlsbad, Calif.) and grown overnight on LB agar plates containing 100 µg/ml of ampicillin. Transformed colonies were harvested into LB medium and used to inoculate 3×2 liters of LB medium containing ampicillin in 3-liter baffled flasks. The flasks were rotated at 120 RPM for 4-5 hours at 37° C. until the turbidity reached approximately 0.8 $OD_{600}$ units. Recombinant protein expression was induced with the addition of IPTG to 1 mM, and the flasks were incubated with shaking for 2 hours. Cells were concentrated by centrifugation, washed once in PBS, and suspended in 35 ml of Binding Buffer (20 mM Sodium Phosphate, 500 mM Sodium Chloride, pH 7.8) containing 7M Guanidine-HCL and set at −80° C. The suspension was thawed, sonicated (3×20 second pulses using a Sonic Dismembrator 550 at a setting of 8), and centrifuged at 32,000×g for 30 minutes. The His-tagged proteins were then isolated using Ni-NTA-agarose (Qiagen Inc., Valencia, Calif.), as directed by the manufacturer. The isolated proteins were dialyzed (12-14K molecular weight cutoff dialysis tubing) overnight against 1 liter of Binding Buffer containing 2 M Urea. The protein concentration was determined and the protein diluted to 1 mg/ml in Binding Buffer containing 2 M Urea and stored frozen at −80° C.

Example 3

Protein Determination and SDS-PAGE:

Total protein was determined by the Bradford Method, Bradford, M., Protein reaction with dyes, Anal. Biochem. 72:241-247 (1976), using dye and Bovine Gamma Globulin standards from Bio-Rad Laboratories (Hercules, Calif.). SDS-PAGE analysis was carried out using Invitrogen Life Technologies NuPAGE 4-12% Bis-Tris precast polyacrylamide gels and run on their Novex Mini-Cell electrophoresis apparatus. Separated proteins were stained with 0.25% Brilliant Blue R (Sigma Chemical Co., St. Louis, Mo.).

Example 4

ELISA Reactions:

Recombinant antigens were diluted to 10 µg/ml in Glycine Buffer (0.05 M Glycine, pH 9, 137 mM NaCl), 0.1 ml/well was added to Nunc F8 Maxisorb Immuno Module Elisa strips, and the strips were incubated overnight at 4° C. The wells were washed 3× with 0.3 ml/well of TBS (0.05 M Tris, pH 7.4, 137 mM NaCl) containing 0.05% Tween 20. Then 0.2 ml/well of blocking buffer was added and the wells incubated at room temperature for 40 minutes. For IgG detection, the blocking buffer was TBS+5% Milk Diluent/ Blocking Solution from Kirkegaard and Perry Laboratories, Inc. (Gaithersburg, Md.). For IgM detection, the blocking buffer was TBS+10% Normal Goat Serum (Hyclone, Logan, Utah). Sera were diluted 100-fold for IgG assays and 50-fold for IgM assays in their respective blocking buffers. The secondary antibody used in the ELISA reactions was HRP-conjugated goat anti-human IgG or IgM (American Qualex, San Clemente, Calif.) diluted 1,000-fold in blocking buffer. The substrate was o-phenylenediamine dihydrochloride (Sigma Chemical Co., St. Louis, Mo.) used at 3 mg/ml in citrate buffer (0.024 M Citric Acid, 50 mM $Na_2HPO_4$, pH 5). For all assays, blank wells were prepared exactly as they were for the test wells except that no antigen was present in the coating buffer. At the conclusion of the assay, the absorbance value from each blank well was subtracted from that of their corresponding test well, yielding a net absorbance value for each individual serum tested.

For the initial testing of the developed antigens, control sera from LD positive patients, as well as LD-negative subjects, were generously supplied by MarDX Diagnostics, Inc. (Carlsbad, Calif.). These control sera had been determined by MarDx to be LD IgG and IgM positive or LD negative using their "Marblot" Western blot assays. In addition, sera from healthy subjects with no known history of LD were obtained locally and designated "in-house" negative control sera. These were confirmed negative by Western blot testing or by ELISA using *B. burgdorferi* B31 lysates as antigen (not shown). Well characterized test panels of LD-negative subjects and LD-positive patient sera were provided by the CDC (Fort Collins, Colo.). The acquisition and acceptance of these sera by the CDC for use in Lyme disease diagnostic test development and evaluation was as described in Molins et al., supra. The LD panels from the CDC were supplied in numbered tubes only. The final key was not provided until after the test results were recorded.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly, and use may be made without departing from the principles and concepts set forth herein.

The subject matter claimed is:

1. A recombinant protein consisting essentially of a *Borrelia burgdorferi* decorin-binding protein A (dbpA) peptide and a *Borrelia burgdorferi* C6 peptide.

2. The recombinant protein of claim 1 consisting essentially of a sequence as set forth as SEQ ID NO:10.

3. A method for detecting anti-*Borrelia burgdorferi* antibodies in a patient, the method comprising:
   (a) obtaining a serum or plasma sample from a human patient; and
   (b) detecting whether anti-*Borrelia burgdorferi* antibodies are present in the serum or plasma sample by contacting the serum or plasma sample with a dbpA/C6 recombinant protein consisting essentially of a *Borrelia burgdorferi* dbpA peptide and a *Borrelia burgdorferi* C6 peptide, and
   (c) detecting binding between the anti-*Borrelia burgdorferi* antibodies and the dbpA/C6 recombinant protein.

4. The method of claim 3 wherein the dbpA/C6 recombinant protein consists essentially of a sequence as set forth as SEQ ID NO:10.

* * * * *